United States Patent [19]

Kumar et al.

[11] Patent Number: 5,006,571
[45] Date of Patent: Apr. 9, 1991

[54] DENTURE ADHESIVE COMPOSITION

[75] Inventors: Lori D. Kumar, Princeton; Alexander M. Schobel, Whitehouse Station, both of N.J.

[73] Assignee: Warner-Lambert Company, Morris Plains, N.J.

[21] Appl. No.: 455,703

[22] Filed: Dec. 21, 1989

[51] Int. Cl.$^5$ .................. C09J 101/26; C09J 135/08; A61C 13/23
[52] U.S. Cl. ...................................... 523/120; 524/45; 524/558
[58] Field of Search ................... 523/120; 524/45, 558

[56] References Cited

U.S. PATENT DOCUMENTS

| | | | |
|---|---|---|---|
| 3,736,274 | 5/1973 | Schoenholz | 523/120 |
| 3,868,432 | 2/1975 | Keegan | 523/120 |
| 4,373,036 | 2/1983 | Chang | 523/120 |
| 4,910,247 | 3/1990 | Haldar | 523/120 |

Primary Examiner—C. Warren Ivy
Attorney, Agent, or Firm—Charles A. Gaglia, Jr.

[57] ABSTRACT

A denture adhesive base composition comprising a substantially anhydrous mixture of a mixed Na/Ca salt of methyl vinyl ether-maleic acid, sodium carboxymethylcellulose, and a trivalent cation. A denture adhesive composition including this base composition is provided, as well as a method for formulating the novel adhesives of the invention.

34 Claims, No Drawings

DENTURE ADHESIVE COMPOSITION

BACKGROUND OF THE INVENTION

1. Field of the Invention

This invention relates to denture adhesives or stabilizers, and particularly to an improved anhydrous denture adhesive composition.

2. Description of the Prior Art

Traditionally, adherent powders used to secure dentures within the mouth were prepared from such materials as finely powdered natural gums, i.e. karaya, acacia or tragacanth gum. These materials have the particular property of swelling to many times their original volume upon the addition of water to form a gelatinous or mucilaginous mass. Denture adhesive powders may be a combination of one or more natural gums, generally flavored with pleasant tasting volatile oils. Many other additives may also be included, such as antiseptics, stabilizers, bactericides, special deodorants, plasticizing agents, fillers, coloring agents, and the like.

Cream forms of the denture adherent, prepared from finely ground particles of the natural gums dispersed in a cream base, are also available and may be used instead of the powder compositions. In any event, when wet with water, the natural gum in either the cream or powder formulation expands to become a viscous gel which acts as a cushion and an adherent between the denture plate and the gum tissue.

While these relatively simple formulations are effective in securing dentures within the oral cavity for a short period of time, generally more than one application of adhesive per day is necessary. This is, at best, inconvenient and therefore, most undesirable.

In recent years, there have been numerous improvements in the above-described simple denture adhesive formulations. For example, U.S. Pat. No. 3,736,274 discloses a denture adhesive containing three essential ingredients: a maleic anhydride and/or acid copolymer (with a lower alkyl vinyl ether), a polymeric N-vinyl lactam, and sodium carboxymethylcellulose (CMC), preferably incorporated into a diluent such as petrolatum and/or mineral oil. The patent discloses that the CMC acts in a way to prevent the maleic anhydride copolymer N-vinyl lactam complex from precipitating when placed in water.

U.S. Pat. No. 4,280,936 discloses a denture adhesive comprising sodium carboxymethylcellulose and poly (ethylene oxide) homopolymer in a mineral oil base.

U.S. Pat. No. 4,514,528 is directed to a hydrophilic denture adhesive which consists of an admixture of mixed, partial salts of lower alkyl vinyl ether-maleic anhydride-type copolymers with either sodium carboxymethylcellulose or poly (ethylene oxide) homopolymer or both in a hydrophilic vehicle.

U.S. Pat. No. 4,518,721 discloses a denture adhesive which consists of sodium carboxymethylcellulose and poly (ethylene oxide) in a hydrophilic vehicle comprising certain polyethylene gylcols and, optionally, glycerin.

U.S. Pat. No. 4,569,955 discloses a denture adhesive containing an adhesive polymeric fraction comprising an admixture of mixed, partial salts of lower alkyl vinyl ether-maleic anhydride-type copolymers with sodium carboxymethylcellulose in a mineral oil vehicle thickened with polyethylene having a molecular weight of 1,000 to 21,000.

U.S. Pat. No. 4,373,036 discloses a denture fixative composition containing a dentally acceptable excipient and an effective fixative amount of a fixative mixture comprising hydroxypropyl cellulose and at least one partially neutralized alkyl vinyl ether-maleic acid or anhydride copolymer, optionally partly crosslinked, or a partially neutralized, optionally partly crosslinked polyacrylic acid or a precursor combination of the copolymer or polyacrylic acid, neutralizing agents, and optionally crosslinking agents such as calcium and magnesium.

U.S. Pat. No. 4,521,551 discloses a denture fixative composition containing denture fixative excipients and as the denture fixative, a water soluble partially neutralized alkyl vinyl ether-maleic acid or anhydride copolymer, optionally partly crosslinked with a polyhydroxyl compound, and at least one hydrophilic polymer, preferably sodium carboxymethylcellulose, polyethylene oxide or hydroxypropyl guar.

While the above denture adhesives provide some improvement over simple formulations containing only finely powdered natural gums, it is generally recognized that no one product has yet been developed which can accommodate over a long period of time, the many variations in temperatures, pH and mechanical agitation which are quite normal in the oral cavity.

It has now been found that the denture adhesive of this invention will provide superior adherent properties over prolonged periods of time and under unusually varied conditions, without the disadvantages characteristic of previously known products.

SUMMARY OF THE INVENTION

The novel denture adhesives formed according to the present invention are generally prepared by mixing a denture adhesive base composition with additional materials to produce denture adhesive compositions which, whether formulated in powder or paste form, exhibit excellent properties as denture stabilizers.

Applicants have unexpectedly discovered a denture adhesive base composition comprising a substantially anhydrous mixture of a mixed Na/Ca salt of methyl vinyl ether-maleic acid, sodium carboxymethylcellulose, and a trivalent cation.

In one preferred embodiment of the invention, it has been unexpectedly discovered that a denture adhesive composition can be formed which comprises a substantially anhydrous mixture of from about 40 to about 65 percent by weight, based on the total weight of the denture adhesive composition, of a denture adhesive base composition containing a mixed Na/Ca salt of methyl vinyl ether-maleic acid, sodium carboxymethylcellulose, and a trivalent cation.

In another preferred embodiment, it has been unexpectedly discovered to form a denture adhesive composition comprising a substantially anhydrous mixture of:

(a) from about 40 to about 65 percent by weight, based on the total weight of the denture adhesive composition, of a denture adhesive base composition containing a mixed Na/Ca salt of methyl vinyl ethermaleic acid, sodium carboxymethylcellulose and a trivalent cation; and (b) from about 35 to about 60 percent by weight, based on the total weight of the denture adhesive composition, of additional materials selected from the group consisting of waxes, oils, preservatives, flavoring agents, colorants, sweetening agents, viscosity modifiers and mixtures thereof.

In an especially preferred embodiment it has been unexpectedly discovered to form a denture adhesive composition comprising a substantially anhydrous mixture of:

(a) from about 0.1 to about 5.0 percent by weight, based on the total weight of the denture adhesive composition, of a trivalent cation;

(b) from about 20 to about 45 percent by weight, based on the total weight of the denture adhesive composition, of a mixed Na/Ca salt of methyl vinyl ether-maleic acid;

(c) from about 12 to about 35 percent by weight, based on the total weight of the denture adhesive composition, of sodium carboxymethylcellulose; and (d) additional materials in an amount sufficient to yield a denture adhesive composition having a total weight equal to 100 percent by weight of the total denture adhesive composition.

The invention also involves a method for preparing these novel denture stabilizers.

In one preferred embodiment, a method for preparing a denture adhesive base composition comprises:

(a) preparing a substantially anhydrous mixture of a mixed Na/Ca salt of methyl vinyl ether-maleic acid, sodium carboxymethylcellulose and a trivalent cation;

(b) forming a denture adhesive base composition including said mixture; and (c) recovering said denture adhesive base composition.

DESCRIPTION OF THE INVENTION

Applicants have unexpectedly discovered a novel denture adhesive base composition comprising a substantially anhydrous mixture of a mixed Na/Ca salt of methyl vinyl ether-maleic acid, sodium carboxymethylcellulose and a trivalent cation.

Denture adhesive compositions formed with the above-described denture adhesive base composition yield a product which provides surprising good performance as a denture adhesive. Specifically, denture adhesives of the present invention require fewer applications per day, exhibit increased holding power, denture cushioning and duration of holding, reduced oozing of components, possess improved extrusion properties, and provide greater consumer confidence of product function.

The invention comprises a unique combination of three essential components, namely a mixed Na/Ca salt of methyl vinyl ether-maleic acid, sodium carboxymethylcellulose and a trivalent cation. In the absence of any of these components from the formulations of this invention, compositions may be prepared which do not exhibit the enhanced effect achieved from this combination.

The mixed Na/Ca salt of methyl vinyl ether-maleic acid utilized in the present formulations is a commercially available copolymeric material known in the art. The copolymer comprises units of alkyl vinyl ether reacted with maleic anhydride. The anhydride form is then converted to the acid or salt form. The mixed Na/Ca salt of methyl vinyl ether-maleic acid functions as the main adhesive component of the instant formulations. Other less preferred salts include the calcium, sodium, potassium salts of methyl vinyl ether-maleic acid, its partial salts, and mixtures thereof. These salts are known to be used in sufficient amounts to react with up to 100% of the carboxyl groups in the material and can be used in amounts to react with about 10 to 70% of the free carboxyl groups.

The copolymer is used in the denture adhesive base formulations of this invention in amounts of about 39.6% to about 73% by weight, and preferably in amounts of about 44.5% to about 69% by weight, based on the weight of the denture adhesive base composition. Amounts above about 73% form unacceptably hard formulations, whereas amounts below about 39.6% lack acceptable adhesive properties.

The second essential component is sodium carboxymethylcellulose which is a commercially available synthetic gum derived from cellulose, and generally comprises an anionic, water-soluble, long chain polymer. The particle size of the sodium carboxymethylcellulose utilized in the present invention is not critical, but preferably comprises material which is 60 mesh (U.S. standard mesh size) or smaller.

The sodium carboxymethylcellulose is used in amounts of about 25% to about 60% by weight and preferably in amounts of about 25% to about 55% by weight of the denture adhesive base composition. Such amounts are suitable to prepare a stable base composition which does not ooze when the sodium carboxymethylcellulose is combined with the trivalent cation as described herein. In the absence of adequate crosslinking unacceptable formulations are prepared which are not suitable for use.

The third essential component of the invention is a trivalent cation and preferably a metal cation. The most preferred material is aluminum. The source of the cations is not critical except to the extent that they are readily available in the presence of water of hydration, such as the water present in saliva to enable the cation to be solubilized and react with the sodium carboxymethylcellulose.

More particularly, the trivalent cation functions in this invention as a crosslinking or complexing agent for the sodium carboxymethylcellulose, thus rendering this cellulose derivative insoluble within the adhesive copolymer matrix. Once the reaction occurs, the denture adhesive formulation becomes more cohesive and resembles a firm moldable mass which has a reduced oozing tendency. In addition, the sodium carboxymethylcellulose in the absence of being crosslinked or complexed tends to swell in the formulation and leaks out when the formulation is used. Such uncrosslinked formulations also exhibit a sticky, gummy mass resembling taffy, which products do not resume their shape when used. Crosslinking of this component eliminates this deficiency and results in the formation of a firm, essentially non-leachable/degradable, denture adhesive formulation which will retain its shape when applied to the denture and retained in the oral cavity.

The trivalent cations may be derived from materials that form the cation in the presence of water, and thus preferred sources of cations are compounds that are water-soluble. An optional component is a divalent cation which aids in adjusting the cohesivity of the denture adhesive. Such materials may be employed in amounts of about 0.1% to about 5% by weight of the denture adhesive composition.

Exemplary, non-limiting materials may be selected from the group consisting of aluminum sulfate, magnesium sulfate, aluminum ammonium sulfate, aluminum ammonium chloride, dihydroxy aluminum sodium carbonate, aluminum acetate, magnesium acetate, magnesium chloride, magnesium citrate (dibasic), magnesium formate, magnesium gluconate, magnesium oxide, magnesium phosphate (monobasic), aluminum potassium sulfate, aluminum sodium sulfate, and mixtures thereof.

The trivalent cations are used in sufficient amounts to crosslink the sodium carboxymethylcellulose rendering this material insoluble. Suitable amounts may range from about 0.4% to about 7.0% and preferably from about 0.5% to about 6.0% by weight, based on the weight of the denture adhesive base composition.

When using dihydroxy aluminum sodium carbonate, it is necessary to include a food grade acid in the formulation to aid in the release of the aluminum from the composition. Exemplary acids include citric acid, malic acid, tartaric acid, fumaric acid and so forth. When used, the acids are present in amounts of about 0.5% to about 4% by weight of the denture adhesive composition.

When these three components are intermixed, a denture adhesive base composition is formed which exhibits superior characteristics as a denture stabilizer when incorporated into a denture adhesive composition.

The denture adhesive base composition may comprise from about 0.4 to about 7.0 percent by weight trivalent cation, from about 39.6 to about 73 percent by weight of a mixed Na/Ca salt of methyl vinyl ether-maleic acid, and from about 25 to about 60 percent by weight sodium carboxymethylcellulose, based on the total weight of the denture adhesive base composition.

Preferably, the denture adhesive base composition comprises from about 0.5 to about 6.0 percent by weight trivalent cation, from about 44.5 to about 69.0 percent by weight of a mixed Na/Ca salt of methyl vinyl ether-maleic acid, and from about 25.0 to about 55.0% by weight sodium carboxymethylcellulose, based on the total weight of the denture adhesive base composition.

The denture adhesive base compositions are useful to prepare denture adhesive compositions. According to the invention, a denture adhesive composition is provided which comprises a substantially anhydrous mixture of from about 40 to about 65 percent by weight, based on the total weight of the denture adhesive composition wherein the denture adhesive base composition contains three essential components, (a) a mixed Na/Ca salt of methyl vinyl ethermaleic acid; (b) sodium carboxymethylcellulose; and (c) a trivalent cation.

An optional component that is beneficial when used in the formulations of this invention is a material which pulls water into the formulation when applied to the denture and placed in the oral cavity. Such a material will aid in fully hydrating the formulation, causing full solubilization of the trivalent cation and crosslinking of the sodium carboxymethylcellulose. Exemplary hygroscopic or water-swellable materials include pharmaceutically acceptable disintegrants such as fumed silica, silica gel, crosslinked polyvinylpyrrolidone, starch NF, and ion exchange resins. Such materials when used are preferably employed in amounts of about 0.5 to about 6.0% by weight of the denture adhesive composition.

In addition to the foregoing materials, the denture adhesive composition may be formulated with additional components well known in the denture adhesive art. Such additional materials utilized in the invention may comprise waxes, oils, preservatives, flavoring agents, colorants, sweetening agents, viscosity modifiers and so forth.

The waxes useful in the invention comprise both natural and synthetic waxes and include without limitation animal waxes such as beeswax, lanolin and shellac wax, vegetable waxes such as carnauba, candelilla and bayberry wax, mineral wax such as petroleum waxes including paraffin, and microcrystalline. In general, amounts of about 1% to about 15% by weight of the total denture adhesive composition are usable, with amounts of about 10% to about 25% being preferred.

The oils useful in the invention include without limitation mineral oil, vegetable oil such as corn, soybean, cottonseed, castor, palm and coconut oils and animal oil such as fish oil, and oleic acid. In general, amounts of about 1% to about 30% by weight of the total denture adhesive composition are usable, with amounts of about 10% to about 25% being preferred.

Flavoring agents well known to the denture adhesive art may be added to the compositions of the instant invention. These flavoring agents may be chosen from synthetic flavor oils and/or oils derived from plants, leaves, flowers, fruits and so forth, and combinations thereof. Representative flavor oils include: spearmint oil, cinnamon oil, oil of wintergreen (methylsalicylate) and peppermint oils. Also useful are artificial, natural or synthetic fruit flavors such as citrus oil including lemon, orange, grape, lime and grapefruit, and fruit essences including apple, strawberry, cherry, pineapple and so forth. The flavoring agent may be a liquid, spray dried, encapsulated, adsorbed on a carrier and mixtures thereof. A preferred flavoring agent is peppermint oil. The amount of flavoring agent utilized may vary depending on such factors as flavor type, adhesive formulation and strength desired. In general, amounts of about 0.01% to about 5.0% by weight of the total denture adhesive composition are usable, with amounts of about 0.05% to 0.15% being preferred.

Preservatives which may be used in the denture adhesive formulations of the invention include those known antimicrobial agents conventionally employed in the art, such as benzoic acid and sodium benzoate; the parabens; sorbic acid and sorbates; propionic acid and propionates; acetic acid and acetates; nitrates and nitrites; sulfur dioxide and sulfites; antibiotics; diethyl pyrocarbonate; epoxides; hydrogen peroxide; and phosphates. The parabens include the methyl, ethyl, propyl, and butyl esters of parahydroxybenzoic acid. Methyl paraben and propyl paraben are the preferred preservatives of the invention, preferably utilized in amounts of about 0.03% to about 0.6% by weight of the total denture adhesive composition.

The denture adhesive compositions may also include the use of sweeteners well known in the art.

The sweetening agent may be selected from a wide range of materials including water-soluble agents, water-soluble artificial sweeteners, and dipeptide based sweeteners, including mixtures thereof. Without being limited to particular sweeteners, representative illustrations encompass:

A. Water-soluble sweetening agents such as monosaccharides, disaccharides and polysaccharides such as xylose, ribose, glucose, mannose, galactose, fructose, dextrose, sucrose, sugar, maltose, partially hydrolyzed starch, or corn syrup solids and sugar alcohols such as sorbitol, xylitol, mannitol, maltitol, hydrogenated starch hydrolysate and mixtures thereof.

B. Water-soluble artificial sweeteners such as the soluble saccharin salts, i.e., sodium or calcium saccharin salts, cyclamate salts, acesulfame-K, sucralose and the like, and the free acid form of saccharin.

C. Dipeptide based sweeteners such as L-aspartyl-L-phenylalanine methyl ester and materials described in U.S. Pat. No. 3,491,131, and the like.

In general, the amount of sweetener will vary with the desired amount of sweetener selected for a particular denture adhesive formulation. This amount may be about 0.001% to about 25% by weight of the final denture adhesive composition.

The colorants useful in the present invention include pigments such as titanium dioxide, and may also include dyes suitable for food, drug and cosmetic applications. These colorants are known as F.D. & C. dyes. The materials acceptable for the foregoing spectrum of use are preferably water-soluble. Illustrative examples include indigo dye, known as F.D. & C. Blue No. 2, which is the disodium salt of 5,5'-indigotin-di-sulfonic acid. Similarly, the dye known as F.D. & C. Green No. 1, comprises a triphenylmethane dye and is the monosodium salt of the 4-[4-N-ethyl-p-sulfobenzylamino) diphenylmethylene]-[1-N-ethyl-N-p-sulfonium-benzyl)-2,5-cyclohexadienimine]. A preferred colorant is F.D. & C. Red No. 3. A full recitation of F.D. & C. and D. & C. colorants and their corresponding chemical structures may be found in the Kirk-Othmer Encyclopedia of Chemical Technology, 3rd Edition, in Volume 6, at pages 561–595. In general, colors when used are employed in amounts of about 0.005% to about 0.5% by weight of the denture adhesive composition.

The viscosity modifiers useful herein include polyethylene and its derivatives, quaternary ammonium compounds and similar agents, starches, gums and casein gelatin.

These viscosity modifiers may be further defined as they relate to each of the two components of the final denture adhesive composition namely: (a) the vehicle, and (b) the gum component.

When a mineral oil vehicle is employed, polyethylene may be optionally used as a gelling agent to provide a "synthetic petrolatum" vehicle, and thus is used to adjust the extrusion (application) properties of the finished composition. Polyisobutylene may also be used in conjunction with polyethylene to further enhance the viscosity properties of the vehicle. Alternatively, a stock petrolatum, with or without mineral oil, may be employed depending upon the specific handling qualities which are desired in the final product. A particularly preferred combination involves use of petrolatum in amounts of about 10% to about 30%, and a light mineral oil in amounts of about 10% to about 30% by weight of the denture adhesive composition in order to prepare an easily extrudable formulation having a cream like consistency. When used together, these components are preferably used in substantially equivalent amounts by weight.

The remaining viscosity modifiers useful in the present invention (quaternary ammonium compounds, sodium carboxymethylcellulose, etc.) belong to the gum block of the denture adhesive. These agents have an impact on the extrusion qualities of the adhesive, but are functionally dormant until they are activated by saliva in the mouth.

In another aspect of the invention, a denture adhesive composition is provided which comprises a substantially anhydrous mixture of:

(a) from about 40 to about 65 percent by weight, based on the total weight of the denture adhesive composition, of a denture adhesive base composition containing a mixed Na/Ca salt of methyl vinyl ethermaleic acid, sodium carboxymethylcellulose and trivalent cation; and (b) from about 35 to about 60 percent by weight, based on the total weight of the denture adhesive composition, of additional materials selected from the group consisting of waxes, oils, preservatives, flavoring agents, colorants, sweetening agents, viscosity modifiers and mixtures thereof.

In an especially preferred aspect of the invention, a denture adhesive composition is formed which comprises a substantially anhydrous mixture of:

(a) from about 0.1 to about 5.0 percent by weight, based on the total weight of the denture adhesive composition, of a trivalent cation;

(b) from about 20 to about 45 percent by weight, based on the total weight of the denture adhesive composition, of a mixed Na/Ca salt of methyl vinyl ether-maleic acid;

(c) from about 12 to about 35 percent by weight, based on the total weight of the denture adhesive composition, of sodium carboxymethylcellulose; and (d) additional materials in an amount sufficient to yield a denture adhesive composition having a total weight equal to 100 percent by weight of the total denture adhesive composition.

The denture adhesive compositions may be in the form of a paste or powder mixture. The means for preparing such formulations is well known in the denture adhesive art.

In a preferred aspect of the invention, the denture adhesive base composition may further include at least one cream base material selected from the group consisting of petrolatum, natural and synthetic oils and mixtures thereof.

In another preferred aspect of the invention, the denture adhesive base composition may further include a cream base material which is a combination of mineral oil with a minor amount of polyethylene wax having an average molecular weight of 1,000 to 20,000.

In another preferred aspect of the invention, the denture adhesive base composition may further include non-toxic, powdered, excipient materials.

The denture adhesive compositions and denture adhesive base compositions of this invention may be formulated to contain the trivalent cation, mixed Na/Ca salt of methyl vinyl ether-maleic acid, and sodium carboxymethylcellulose in either powder or paste form. In the powder form, the components are admixed with the optional flavoring agents and colorants, together with other non-essential ingredients such as non-toxic anti-caking agents (silica, magnesium stearate, talcum powder or the like). The mixture of ingredients is thoroughly agitated or stirred to yield a generally homogenous intermixing of all components. In the paste formulations, the trivalent cation, mixed Na/Ca salt of methyl vinyl ether-maleic acid and sodium carboxymethylcellulose are admixed with petrolatum, along with the previously described waxes, oils, preservatives, flavoring agents, colorants, sweetening agents, viscosity modifiers and so forth.

A particularly preferred paste or cream formulation is prepared by utilizing as the cream or paste base, the product of U.S. Pat. No. 3,215,599, the disclosure of which is incorporated herein by reference. The cream or paste base of this patent is characterized as a mixture of white petroleum oil with a minor amount of a polyethylene wax having an average molecular weight of 1,000 to 20,000. This product is described as having emollient properties, useful in the formulation of medicaments where absorption of the medicaments by the skin is of paramount importance. Denture adhesive creams formulated with this petroleum oil/polyethylene wax blend as the paste or cream base display unusually good stability, extrudability and product appearance.

The method for preparing the denture adhesive compositions according to the present invention, whether formulated as a powder, paste or cream employs conventional types of mixing equipment which are known in the art for blending, heating and cooling solids and liquids.

The method for preparing the denture adhesive base compositions and denture adhesive compositions containing the same may be conveniently prepared by mixing the components until a homogeneous mixture is obtained and recovering the resulting product. Preferably the base composition is prepared as a preblended formulation which can be mixed with the remaining components used to prepare the final formulation. Mixing is conveniently performed at temperatures suitable to melt the components to be blended. For example, if polyethylene and mineral oil are to be employed such material may be heated to temperatures from about 50° to 110° C., and are preferably cooled prior to blending with the base preblend. Flavoring agents may be added to the preblend and/or the wax/oil mixture prior to mixing in the final mixture.

Whether formulated as a powder, paste or cream, the denture adhesive compositions and base compositions of this invention, When applied to dentures and exposed to moisture, hydrate to form adhesive compositions which exhibit unexpectedly superior characteristics in comparison with denture adhesives of the prior art. Once formulated the compositions may be used or stored for future use.

The following examples are given to illustrate the invention, but are not deemed to be limiting thereof. All percentages given throughout the specification are based on the weight of the denture adhesive base composition or the final denture adhesive composition unless otherwise indicated. All formulations result in compositions having 100% components contained therein.

EXAMPLE 1

This example demonstrates the preparation of a denture adhesive formulation according to the invention.

A denture adhesive cream was prepared from the ingredients recited in Table 1. The formulations were prepared as follows:

A. Weigh mineral oil and petrolatum into a pot, and mix to form a homogenous mixture while raising the temperature to 90°–95° C. Check to assure complete solution. With continued mixing, cool to at least 45° C.

B. Add methyl paraben and propyl paraben to the mixture from Step A and continue mixing until a homogenous blend is obtained.

C. Preblend the trivalent cation, mixed Na/Ca salt of methyl vinyl ether-maleic acid, sodium carboxymethylcellulose, ethylene oxide polymer disintegrant and color; and add to the above mixture with continued mixing. After about 5 minutes scrape down as needed. Reduce pressure to about 28–29 inches vacuum and mix for about 5–10 additional minutes. The product is removed and stored for use.

The denture adhesive formulations prepared according to the aforementioned procedure when tested provided excellent adhesive and improved holding power. In addition, they possess improved cohesive characteristics with diminished oozing between dentures.

The invention being thus described, it will be obvious that the same may be varied in many ways. Such variations are not to be regarded as a departure from the spirit and scope of the invention and all such modifications are intended to be included within the scope of the following claims.

TABLE 1

| INGREDIENTS | INVENTIVE RUNS | | | | | | |
|---|---|---|---|---|---|---|---|
| | I | II | III | IV | V | VI | VII |
| Petrolatum | 20.4281 | 20.5784 | 20.5784 | 20.1770 | 17.8046 | 18.3256 | 19.1359 |
| Mineral Oil Light | 20.4281 | 20.5784 | 20.5784 | 20.1770 | 17.8046 | 18.3257 | 19.1360 |
| Fumed Silica | 1.4419 | 1.4525 | 1.4525 | 1.4276 | 0.8504 | 0.8753 | 0.9140 |
| Methylvinylether-maleic acid mixed sodium/calcium salt | 28.8397 | 29.0518 | 29.0518 | 28.4852 | 29.3548 | 30.2138 | 31.5499 |
| Sodium carboxymethylcellulose | 24.0331 | 24.2098 | 24.2098 | 23.7376 | 20.8689 | 21.4797 | 22.4295 |
| Dihydroxy Aluminum Sodium Carbonate | 0.4867 | — | — | — | — | — | — |
| Fumaric Acid | 2.1660 | — | — | — | — | — | — |
| Aluminum Ammonium Sulfate | — | 1.9367 | — | — | — | — | — |
| Magnesium Sulfate | — | — | — | 2.8845 | 0.3388 | 0.3487 | 2.8560 |
| Aluminum Sulfate | — | — | 1.9367 | 0.9615 | 1.0119 | 1.0415 | 0.9521 |
| Ethylene Oxide Polymer | 1.9227 | 1.9368 | 1.9368 | 1.8992 | 4.5175 | 1.7232 | 1.7993 |
| Peppermint Oil | 0.0752 | 0.0757 | 0.0757 | 0.0742 | 0.0654 | 0.0673 | 0.0703 |
| Methyl Paraben | 0.0480 | 0.0483 | 0.0483 | 0.0474 | 0.0418 | 0.0430 | 0.0450 |
| Propyl Paraben | 0.0961 | 0.0968 | 0.0968 | 0.0949 | 0.0837 | 0.0862 | 0.0900 |
| Color | 0.0344 | 0.0348 | 0.0348 | 20.0339 | 0.0296 | 0.0305 | 0.0319 |
| Disintegrant | | | | | 7.2280 | 7.4395 | 0.9901 |
| | 100.000% | 100.000% | 100.000% | 100.000% | 100.0000% | 100.0000% | 100.0000% |

What is claimed is:

1. A denture adhesive base composition comprising an adhesive copolymer matrix comprising a substantially anhydrous mixture of a mixed Na/Ca salt of methyl vinyl ether-maleic acid copolymer, sodium carboxymethylcellulose and a water soluble material which provides an amount of trivalent cations in water sufficient to crosslink said sodium carboxymethylcellulose and render said sodium carboxymethylcellulose insoluble in said adhesive copolymer matrix.

2. The denture adhesive base composition of claim 1, wherein said trivalent cation is present in amounts of from about 0.4 to about 7.0 percent by weight, based on the total weight of the denture adhesive base composition, said mixed Na/Ca salt of methyl vinyl ether-maleic acid copolymer is present in amounts of from about 39.6 to about 73 percent by weight, based on the total weight of the denture adhesive base composition, and said sodium carboxymethylcellulose is present in amounts of from about 25 to about 60 percent by weight, based on the total weight of the denture adhesive base composition.

3. The denture adhesive base composition of claim 2, wherein said trivalent cation is present in amounts of from about 0.5 to about 6.0 percent by weight, based on the total weight of the denture adhesive base composition, said mixed Na/Ca salt of methyl vinyl ether-maleic acid copolymer is present in amounts of from about 44.5 to about 69 percent by weight, based on the total weight of the denture adhesive base composition, and said sodium carboxymethylcellulose is present in amounts of from about 25 to about 55 percent by weight, based on the total weight of the denture adhesive base composition.

4. The denture adhesive base composition of claim 1, wherein the trivalent cation is aluminum.

5. The denture adhesive base composition of claim 1, wherein the trivalent cation is obtained from a material selected from the group consisting of aluminum sulfate, aluminum ammonium chloride, dihydroxy aluminum sodium carbonate, aluminum acetate, aluminum potassium sulfate, aluminum sodium sulfate, and mixtures thereof.

6. The denture adhesive base composition of claim 1, wherein a divalent cation is employed along with the trivalent cation to aid in adjusting the cohesivity of the denture adhesive.

7. The denture adhesive base composition of claim 6, wherein the divalent cation is obtained from a material selected from the group consisting of magnesium sulfate, magnesium acetate, magnesium chloride, magnesium citrate (dibasic), magnesium formate, magnesium gluconate, magnesium oxide, magnesium phosphate (monobasic), and mixtures thereof.

8. A denture adhesive composition which comprises a substantially anhydrous mixture of from about 40 to about 65 percent by weight, based on the total weight of the denture adhesive composition, of a denture adhesive base composition containing an adhesive copolymer matrix comprising a mixed Na/Ca salt of methyl vinyl ether-maleic acid copolymer, sodium carboxymethylcellulose and a water soluble material which provides an amount of trivalent cations in water sufficient to crosslink said sodium carboxymethylcellulose and render said sodium carboxymethylcellulose insoluble in said adhesive copolymer matrix.

9. The denture adhesive composition of claim 8, further including at least one cream base material selected from the group consisting of petrolatum, natural and synthetic oils and mixtures thereof.

10. The denture adhesive composition of claim 8, further including a cream base material which is a combination of mineral oil with a minor amount of a polyethylene wax having an average molecular weight of 1,000 to 20,000.

11. The denture adhesive composition of claim 8, further including non-toxic, powdered, excipient materials.

12. A denture adhesive composition comprising a substantially anhydrous mixture of:
(a) from about 40 to about 65 percent by weight, based on the total weight of the denture adhesive composition, of a denture adhesive base composition containing an adhesive copolymer matrix comprising a mixed Na/Ca salt of methyl vinyl ether-maleic acid copolymer, sodium carboxymethylcellulose, and a water soluble material which provides an amount of trivalent cations in water sufficient to crosslink said sodium carboxymethylcellulose and render said sodium carboxymethylcellulose insoluble in said adhesive copolymer matrix; and
(b) from about 35 to about 60 percent by weight, based on the total weight of the denture adhesive composition, of additional materials selected from the group consisting of waxes, oils, preservatives, flavoring agents, colorants, sweetening agents, viscosity modifiers and mixtures thereof.

13. The denture adhesive composition of claim 10, wherein the trivalent cation is aluminum.

14. The denture adhesive composition of claim 12, wherein the trivalent cation is obtained from a material selected from the group consisting of aluminum sulfate, aluminum ammonium chloride, dihydroxy aluminum sodium carbonate, aluminum acetate, aluminum potassium sulfate, aluminum sodium sulfate, and mixtures thereof.

15. The denture adhesive composition of claim 12, wherein a divalent cation is employed along with the trivalent cation to aid in adjusting the cohesivity of the denture adhesive.

16. The denture adhesive composition of claim 15, wherein the divalent cation is obtained from a material selected from the group consisting of magnesium sulfate, magnesium acetate, magnesium chloride, magnesium citrate (dibasic), magnesium formate, magnesium gluconate, magnesium oxide, magnesium phosphate (monobasic), and mixtures thereof.

17. A denture adhesive composition comprising a substantially anhydrous mixture of:
(a) a water soluble material which in water provides from about 0.1 to about 5.0 percent by weight, based on the total mixture, of a trivalent action which serves to crosslink sodium carboxymethyl cellulose and to render said sodium carboxymethyl cellulose insoluble in an adhesive copolymer matrix of component (b) below;
(b) from about 20 to about 45 percent by weight, based on the total weight of the denture adhesive composition, of a mixed Na/Ca salt of methyl vinyl ether-maleic acid copolymer;
(c) from about 12 to about 35 percent by weight, based on the total weight of the denture adhesive composition, of sodium carboxymethylcellulose; and
(d) additional materials in an amount sufficient to yield a denture adhesive composition having a total weight equal to 100 percent by weight of the total denture adhesive composition.

18. The denture adhesive composition of claim 17, wherein said additional materials are selected from the group consisting of waxes, oils, preservatives, flavoring agents, colorants, sweetening agents, viscosity modifiers and mixtures thereof.

19. The denture adhesive composition of claim 17, wherein the trivalent cation is aluminum.

20. The denture adhesive composition of claim 17, wherein the trivalent cation is obtained from a material selected from the group consisting of aluminum sulfate, aluminum ammonium chloride, dihydroxy aluminum sodium carbonate, aluminum acetate, aluminum potassium sulfate, aluminum sodium sulfate, and mixtures thereof.

21. The denture adhesive composition of claim 17, wherein a divalent cation is employed along with the trivalent cation to aid in adjusting the cohesivity of the denture adhesive.

22. The denture adhesive composition of claim 21, wherein the divalent cation is obtained from a material selected from the group consisting of magnesium sulfate, magnesium acetate, magnesium chloride, magnesium citrate (dibasic), magnesium formate, magnesium gluconate, magnesium oxide, magnesium phosphate (monobasic), and mixtures thereof.

23. A method for preparing a denture adhesive base composition comprising:
   (a) preparing an adhesive copolymer matrix comprising a substantially anhydrous mixture of a mixed Na/Ca salt of methyl vinyl ether-maleic acid copolymer, sodium carboxymethylcellulose, and a water soluble material which provides an amount of trivalent cations in water sufficient to crosslink said sodium carboxymethylcellulose and render said sodium carboxymethylcellulose insoluble in said adhesive copolymer matrix;
   (b) forming a denture adhesive base composition including said mixture; and
   (c) recovering said denture adhesive base composition.

24. The method of claim 23, wherein said trivalent cation is present in amounts of from about 0.4 to about 7 percent by weight, based on the total weight of the denture adhesive base composition, said mixed Na/Ca salt of methyl vinyl ether-maleic acid copolymer is present in amounts of from about 39.6 to about 73 percent by weight, based on the total weight of the denture adhesive base composition, and said sodium carboxymethylcellulose is present in amounts of from about 25 to about 60 percent by weight, based on the total weight of the denture adhesive base composition.

25. The method of claim 24, wherein said trivalent cation is present in amounts of from about 0.5 to about 6.0 percent by weight, based on the total weight of the denture adhesive base composition, said mixed Na/Ca salt of methyl vinyl ether-maleic acid copolymer is present in amounts of from about 44.5 to about 69 percent by weight, based on the total weight of the denture adhesive base composition, and said sodium carboxymethylcellulose is present in amounts of from about 25 to about 55 percent by weight, based on the total weight of the denture adhesive base composition.

26. A method for preparing a denture adhesive composition comprising:
   (a) preparing a substantially anhydrous mixture of from about 40 to about 65 percent by weight, based on the total weight of the denture adhesive composition, of a denture adhesive base composition containing an adhesive copolymer matrix comprising a mixed Na/Ca salt of methyl vinyl ether-maleic acid copolymer, sodium carboxymethylcellulose, and a water soluble material which provides an amount of trivalent cations in water sufficient to crosslink said sodium carboxymethylcellulose and render said sodium carboxymethylcellulose insoluble in said adhesive copolymer matrix;
   (b) mixing the denture adhesive base with from about 35 to about 60 percent by weight, based on the total weight of the denture adhesive composition, of additional materials selected from the group consisting of waxes, oils, preservatives, flavoring agents, colorants, sweetening agents, viscosity modifiers and mixtures thereof;
   (c) forming a denture adhesive composition including said denture adhesive base composition; and
   (d) recovering said denture adhesive composition.

27. The method of claim 26, wherein said denture adhesive composition further includes at least one cream base material selected from the group consisting of petrolatum, natural and synthetic oils and mixtures thereof.

28. The method of claim 26, wherein said denture adhesive composition further includes a cream base material which is a combination of mineral oil with a minor amount of a polyethylene wax having an average molecular weight of 1,000 to 20,000.

29. The method of claim 26, wherein said denture adhesive composition further includes non-toxic, powdered, excipient materials.

30. The method of claim 26, wherein said additional materials are selected from the group consisting of waxes, oils, preservatives, flavoring agents, colorants, sweetening agents, viscosity modifiers and mixtures thereof.

31. The denture adhesive composition of claim 26, wherein the trivalent cation is aluminum.

32. The method of claim 26, wherein the trivalent cation is obtained from a material selected from the group consisting of aluminum sulfate, aluminum ammonium sulfate, aluminum ammonium chloride, dihydroxy aluminum sodium carbonate, aluminum acetate, aluminum potassium sulfate, aluminum sodium sulfate, and mixtures thereof.

33. The method of claim 26, wherein a divalent cation is employed with the trivalent cation to aid in adjusting the cohesivity of the denture adhesive.

34. The denture adhesive composition of claim 33, wherein the divalent cation is obtained from a material selected from the group consisting of magnesium sulfate, magnesium acetate, magnesium chloride, magnesium citrate (dibasic), magnesium formate, magnesium gluconate, magnesium oxide, magnesium phosphate (monobasic), and mixtures thereof.

* * * * *